United States Patent [19]
Nigam

[11] Patent Number: 5,081,987
[45] Date of Patent: Jan. 21, 1992

[54] IMPLANTABLE MEDICAL DEVICE FOR STIMULATING A PHYSIOLOGICAL EVENT OF A LIVING BEING WITH STIMULATION INTENSITY ADAPTABLE TO PHYSICAL ACTIVITY OF THE LIVING BEING

[75] Inventor: Indra Nigam, Sundbyberg, Sweden

[73] Assignee: Siemens Aktiengesellschaft, Munich, Fed. Rep. of Germany

[21] Appl. No.: 492,828

[22] Filed: Mar. 13, 1990

[30] Foreign Application Priority Data

Mar. 13, 1989 [EP] European Pat. Off. ........ 89104401.8

[51] Int. Cl.⁵ .......................................... A61N 1/362
[52] U.S. Cl. .................................. 120/419 PG
[58] Field of Search .................... 128/419 PG

[56] References Cited

U.S. PATENT DOCUMENTS 4,932,408  6/1990  Schaldach .................... 128/419 PG

FOREIGN PATENT DOCUMENTS 0080348  6/1983  European Pat. Off. .
0199224  9/1986  European Pat. Off. .
0225839  6/1987  European Pat. Off. .
0228985  7/1987  European Pat. Off. .
2026870  2/1980  United Kingdom .

*Primary Examiner*—William E. Kamm
*Assistant Examiner*—Scott M. Getzow
*Attorney, Agent, or Firm*—Hill, Van Santen, Steadman & Simpson

[57] ABSTRACT

An implantable medical device comprising means for stimulating physiological event of a living being with a stimulation intensity adaptable to the physical activity of the living being in view of analysis of a signal generated by a sensor means corresponding to the physical activity of the living being. The device includes a memory optionally operable in a write mode or a read mode to which, in the write mode, data corresponding to the chronological curve of the signal of the sensor means can be supplied for storage and, in the read mode, can be recalled for telemetric transmission to a separate data processing means.

9 Claims, 1 Drawing Sheet

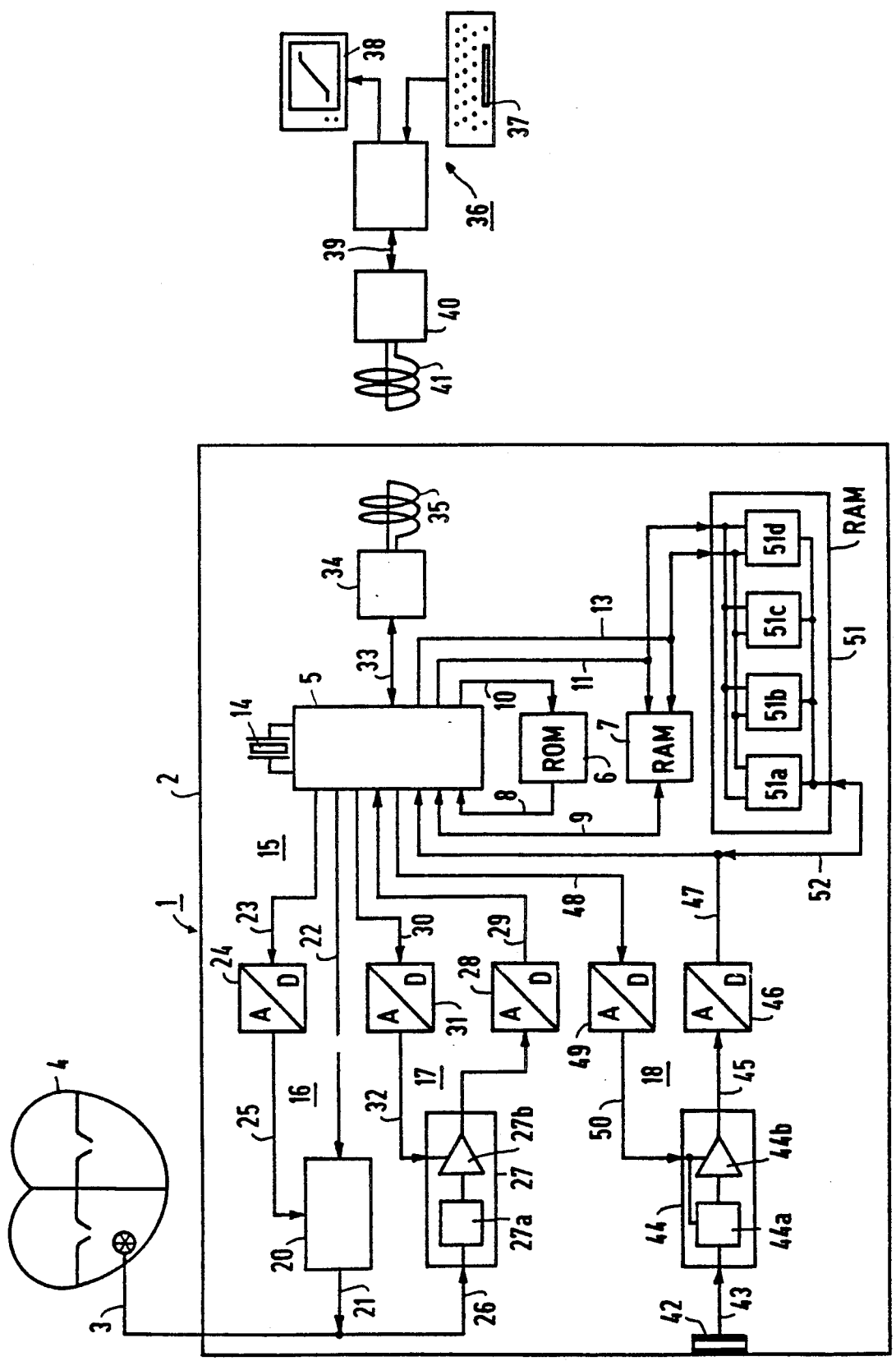

IMPLANTABLE MEDICAL DEVICE FOR STIMULATING A PHYSIOLOGICAL EVENT OF A LIVING BEING WITH STIMULATION INTENSITY ADAPTABLE TO PHYSICAL ACTIVITY OF THE LIVING BEING

BACKGROUND OF THE INVENTION

The invention is directed to a medical device implantable into the body of a living being, comprising means for stimulating a physical event of the living being with variable stimulation intensity and with automatic adjustment means for adapting the stimulation intensity to the physical activity of the living being that set the stimulation intensity with reference to a signal of a sensor means corresponding to the physical activity of the living being, whereby data corresponding to the chronological course of the signal of the sensor means can be telemetrically transmitted from the medical device to a separate data processing means. The term "stimulation intensity" is to be understood to include the duration, the frequency, the repetition rate, the amplitude, etc., with which the means for stimulation are activated, individually and/or in any combination as a measure for the stimulation intensity.

A heart pacemaker of this type is known, wherein the stimulation frequency with which the heart pacemaker stimulates the heart given the absence of natural heart beats is variable depending on the physical activity of the living being. A temperature sensor can be present as a sensor means, this sensor means acquiring the body temperature of the living being wearing the heart pacemaker as a measure for the existing physical activity of the living being.

Since adjustment means that undertake the automatic adaptation of the stimulation frequency to the physical activity of the living being are programmable, there is the possibility of taking the individual requirements of the living being into consideration on the basis of appropriate programming of the adjustment means. In the known heart pacemaker, this occurs in that the living being wearing the heart pacemaker is subjected to a defined physical stress. Data corresponding to the chronological curve of the body temperature thereby measured are telemetrically transmitted to a mini-computer which stores them. There is then the possibility of simulating the reaction of the adjustment means to the stored temperature profile corresponding to a defined physical stress, simulating this on the basis of the correspondingly programmed mini-computer. Various programmings of the adjustment means can thereby be simulated in order to be able to find a programming adapted to the individual requirements of the respective living being. When this has occurred, the data corresponding to the appropriate programming of the adjustment mean are telemetrically transmitted from the data processing means to the heart pacemaker.

It is considered disadvantageous in practice, however, that the living being must again be subjected to a physical stress every time when the programming of the adjustment means is to be checked or modified, the living being being subject to this physical stress in order to acquire the data required for the simulation of the function of the adjustment means. It is also considered disadvantageous that the living being must be in the immediate proximity of the mini-computer during the physical stress or must wear a reception means connected to the mini-computer via a cord, so that the freedom of mobility of the living being is restricted while the living being is being subjected to the physical stress.

SUMMARY OF THE INVENTION

The invention provides a device of the type set forth above wherein freedom of mobility of the living being is not noticeably restricted during the time span when data corresponding to a chronological course of a signal of a sensor means are acquired.

To this end, in an embodiment, the invention provides an implantable device containing a memory optionally operable in write or read modes to which data corresponding to the chronological course of the signal of the sensor means can be supplied for storing in the write mode, and from which the data can be recalled in the read mode via telemetric transmission to the data processing means. When the living being in whose body the device is implanted is subjected to a defined physical stress during the defined time span, the data corresponding to the chronological course of the signal of the sensor means during this time span are stored in the memory, if previously switched into the write mode. After switching the memory to the read mode, the data can be telemetrically transmitted to the data processing means at an arbitrary, later time.

It can be appreciated that no restriction whatsoever of the freedom of mobility of the living being is required in the device of the invention while the living being is being subjected to the physical stress because the living being is not physically tied to a device. Further, there is also the possibility of calling the data corresponding to the chronological course of the signal of the sensor means from the memory of the device as frequently as desired, so that the living being need not be subjected to another physical stress every time when such data are acquired. On the contrary, subjecting the living being to a new stress will only be necessary when the stored data relate to a time so far in the past that they no longer correspond to the current physical condition of the living being.

In another embodiment of the invention, the memory can be selectively switched into the write or read mode via a signal that is telemetrically supplied to the device. The memory preferably includes a plurality of individually addressable memory cells and addressing means for the memory cells so that, after the memory is switched into the write mode, the memory cells are addressed once in a defined sequence and, after the memory is switched into the read mode, again addressed in the defined sequence. Thus, in this manner, the beginning of the defined time span for which data corresponding to the signal of the sensor means are stored, is the time at which the memory is switched into the write mode, so that the beginning of the time span is practically freely selectable. The time at which the stored data are called from the memory for telemetric transmission is likewise arbitrarily selectable, in that the memory is switched into the read mode at the desired time on the basis of a signal preferably telemetrically supplied to the device.

In another embodiment, the invention provides that the addressing means—after the memory is switched into the write mode—continually addresses the memory cells in an addressing cycle in a defined sequence and—after the memory is switched into the read mode—addresses all of the memory cells respectively once in accordance with the defined sequence beginning with the memory cell that follows the memory cell addressed last in the write mode. In this manner, data that correspond to the chronological course of the signal of the sensor means during a defined time span preceding the time the memory is switched into the read mode are respectively stored in the memory.

In another embodiment, the invention provides a device constructed as a heart pacemaker, wherein the means for stimulating physiological event of the living being stimulates the heart activity thereof and the adjustment means adapts the stimulation frequency with which the heart is stimulated as needed by the physical activity of the living being.

In another embodiment, the invention provides that the adjustment means is telemetrically programmable via the data processing means. The advantage of this comes to bear in a medical means of the invention that comprises a medical device constructed in accordance with the invention and a data processing means wherein the function of the adjustment means—based on data corresponding to the chronological course of the signal of the sensor means that are stored in the memory of the device—is simulatable by the data processing means for determining the stimulation intensity based on the physical activity of the living being corresponding to the chronological course of the signal of the sensor means; and wherein the data processing means comprises means for, in particular, graphic portrayal of the stimulation intensity as a function of the physical activity. In this manner, it is possible to first simulate various programmings of the adjustment means in order to then telemetrically program that programming that best corresponds to the requirements of the living being wearing the device.

Further advantages and features of the invention will become more apparent with reference to the following detailed description of the presently preferred embodiments and the accompanying figure of a block circuit diagram of a heart pacemaker system.

BRIEF DESCRIPTION OF THE DRAWING

The sole figure illustrates a heart pacemaker in block diagram form.

DETAILED DESCRIPTION OF THE PRESENTLY PREFERRED EMBODIMENTS

In FIG. 1 there is illustrated a heart pacemaker 1. As will become apparent, the pacemaker 1 can be programmed in accordance with the invention so that a living being in which the pacemaker is implanted need not be tethered while being subjected to a stress test. Further, the pacemaker includes a memory from which data corresponding to a sensor signal can be recalled so that the living being need not be subjected to a stress test every time it is programmed.

The component parts of the heart pacemaker 1 are arranged within a hermetically sealed housing 2. An electrode 3 leads from the heart pacemaker 1, preferably operating in VVI mode, to a heart 4 of a living being where it is implanted within the ventricle.

Among other things, the heart pacemaker 1 comprises a microprocessor 5 to which a read-only memory (ROM) 6 and a write-read random access memory (RAM) 7 are allocated and coupled, these being in communication with the microprocessor 5 via appropriate data lines 8 and 9 and address lines 10 and 11. A line 13 that serves for switching the RAM 7 from write to read mode and vice versa also leads to the RAM 7 from the microprocessor 5.

A program by which all functions of the heart pacemaker 1 are controlled is stored in the ROM 6. Thus, when it is mentioned below that the microprocessor 5 executes a defined function, what is to be understood is that the microprocessor 5 is activated by execution of the program stored in the ROM 6 in view of data stored in the RAM 7 and data for the execution of a particular function that can be supplied from elsewhere, for example, via an input wiring.

A crystal 14 is connected to the microprocessor 5. The crystal 14 serves to generate the clock signals required for the operation of the microprocessor 5 and provides a time reference for the operation of the heart pacemaker 1.

The microprocessor 5 of the heart pacemaker 1 has input/output wiring 15 that comprises a plurality of channels 16, 17, and 18.

The channel 16 supplies the heart 5 with stimulation pulses. The channel 16 therefore includes a stimulation pulse generator 20 with an output line 21 connected to the electrode 3. The stimulation pulse generator 20 is also connected via a line 22 to an output of the microprocessor 5 so that it can be activated for commanding the generation of a stimulation pulse. Digital data that can relate to the shape of the stimulation pulses, for example, defining pulse amplitude and duration are transmitted from the microprocessor 5 via a line 23 to a digital-to-analog (A/D) converter 24. The converter 24 in turn supplies analog control signals corresponding to the digital data to the stimulation pulse generator 20 via a control line 25, these analog control signals setting the stimulation pulse generator 20 such that it generates stimulation pulses having the desired shape.

The channel 17 includes a signal editing circuit 27 connected to the electrode 3 via an input line 26. The signal editing circuit 27 filters and amplifies an electrical signal corresponding to the activity of the heart that is taken from the heart 4 via the electrode 3. The signal editing circuit 27 comprises a filter 27a and an amplifier 27b.

The edited signal is transmitted to an analog-to-digital converter 28 from the output of the signal editing circuit 27. From the analog-to-digital converter 28, digital data is transmitted via a line 29 to a corresponding input of the microprocessor 5, the digital data corresponding to the course of the electrical signal at the output of the signal editing circuit 27. Accordingly, the digital data reflects the electrical activity of the heart 4.

The microprocessor 5 is also connected to a digital-to-analog converter 31 via a line 30. The converter 31 converts the digital data supplied to it by the microprocessor 5 to analog signals which are supplied to the signal editing circuit 27 via a control line 32. The digital data or, respectively, the corresponding analog signals, serve the purpose, for example, of setting the gain of the amplifier 27b or, respectively, of completely blocking the amplifier 27b.

The digital data supplied to the microprocessor 5 via the line 29 are analyzed by the microprocessor 5 which determines whether events that correspond to the occurrence of a natural heart beat are contained in the electrical signal corresponding to the activity of the heart. When the microprocessor 5 detects a natural heart beat, or when it activates the stimulation pulse generator 20 via the line 22 to output a stimulation pulse, the microprocessor 5 begins to operate as a counter and begins to count off a plurality of clock pulses produced by the oscillation of the crystal 14. The resulting count corresponds to a time interval adjustable between an upper and a lower limit. The time interval defines that stimulation frequency with which the heart 4 is stimulated in the absence of natural beats. Accordingly, this interval can be referred to as the stimulation frequency time interval.

When no data are provided to the microprocessor 5 during this time interval via the channel 17, the microprocessor 5 activates the stimulation pulse generator 20 via the line 22 after the expiration of the time interval because no heartbeat is detected. Following the output of a stimulation pulse, the microprocessor 5 again begins to count off a plurality of clock pulses that corresponds to the time interval that defines the stimulation frequency. When, by contrast, the microprocessor 5 detects a natural heartbeat during the course of the time interval, it aborts the described counting process for a further time interval, that is referred to as the refractory time interval. When the refractory time interval has expired and the microprocessor 5 begins the described counting process anew.

The refractory time interval is fundamentally shorter than the time interval that defines the stimulation frequency and is variable, for example, between about 250 and 450 ms. In contrast, the stimulation frequency interval is variable between 400 and 2000 ms.

Further, the refractory time is divided into an absolute refractory time having a fixed duration of, generally, 125 ms and into a variable relative refractory time. The refractory time interval begins to run simultaneously with the time interval that defines the stimulation frequency and is calculated by the microprocessor 5 on the basis of the same counting process that also serves for calculating the time interval that defines the stimulation frequency.

During the absolute refractory time, the amplifier 27b of the signal editing circuit 27 in the channel 17 is completely inhibited, this being achieved in that the microprocessor 5 provides the amplifier 27b with an appropriate control signal via the line 30, the digital-to-analog interface 31, and the control line 32. As a consequence of the complete inhibition of the amplifier 27b, it is not possible for the microprocessor 5 to carry out any detection whatsoever during the duration of the absolute refractory time.

After the expiration of the absolute refractory time, the microprocessor 5 again activates the amplifier 27b, so that it is in the position to detect natural heartbeats. When the microprocessor 5 detects a natural heartbeat during the relative refractory time, it does not abort the counting process for identifying the tim interval that defines the stimulation frequency—as contrasted to detection after the expiration of the refractory time— but continues the counting process and ends it with an activation of the stimulation pulse generator 20. After the detection of a natural heartbeat, however, the microprocessor 5 again starts the full refractory time.

What is achieved from the foregoing is that, given radio-frequency disturbances that lead to misdetections, stimulation pulses having the stimulation frequency defined by the set time interval are generated independently of the appearance of natural heartbeats. Even when the spontaneous heartbeat frequency is so high that natural heartbeats occur within the relative refractory time every time, an output of stimulation pulses ensues with the stimulation frequency defined by the stimulation frequency time interval, i.e., until the spontaneous heartbeat frequency has fallen below a frequency whose period duration corresponds to the set refractory time. Ending defined re-entry tachycardia is possible with this function.

As further illustrated, the microprocessor 5 is connected via a line 33 to a telemetry circuit 34 to which a transmission/reception coil 35 is connected. Thus, the heart pacemaker 1 can exchange data with an external data processing means, e.g., with a personal computer (PC) 36 having a keyboard 37 and a monitor 38, since the PC 36 is connected via a line 39 to a second telemetry circuit 40 to which a transmission/-reception coil 41 is also connected.

For the exchange of data between the heart pacemaker 1 and the PC 36, the transmission/reception coil 41 of the telemetry circuit 40 belonging to the PC 36 is positioned on the body surface of the living being in whom the heart pacemaker 1 is implanted so that the coil 41 is inductively coupled with the transmission/-reception coil 35 of the heart pacemaker 1. It is then possible to supply the PC 36 with the data stored in the ROM 6 and the RAM 7 for checking or, respectively, for checking and modifying the operation of the pacemaker. It is also possible to supply the RAM 7 of the heart pacemaker 1 with modified data or, respectively, additional data from the PC 36.

The channel 18 of the input/output circuit 15 of the microprocessor 5 makes data available to the microprocessor 5 that allow the microprocessor 5 to adapt the time interval that defines the stimulation frequency to the physical activity of the living being in whom the heart pacemaker 1 is implanted, namely with reference to the program stored in the ROM 6. To this end, a piezoelectric pressure sensor 42 is provided that is connected to the wall of the housing 2. For physical activity of the living being, mechanical vibrations in the body of the living being arise due to the motion of the muscles and the like, these mechanical vibrations propagating in the body of the living being as pressure waves and being sensed by the piezoelectric sensor 42 which then converts the pressure waves into electrical signals. The electrical signals generated by the sensor 42, whose amplitude increases with increasing physical activity, are transmitted via a line 43 to a signal editing circuit 44 that contains a filter 44a with following amplifier 44b.

An output signal of the signal editing circuit 44 is transmitted via a line 45 to an analog-to-digital converter 46, for example, an eight-bit converter, whose digital output signals are, in turn, transmitted via a line 47 to the microprocessor 5.

The microprocessor 5 is connected via a line 48 to a digital-to-analog converter 49 that forwards the digital data supplied to it by the microprocessor 5 to the signal editing circuit 44 as corresponding analog signals via a control line 50. The digital data or, respectively, the analog signals corresponding thereto serve the purpose of, for example, setting the gain of the amplifier 34b or modifying the characteristics of the filter 44a.

Based on the chronological curve of the signal generated by the piezoelectric sensor 42 or, respectively, of the corresponding digital data, the microprocessor 5 can vary the time interval that defines the stimulation frequency—in a way similar to that disclosed in European patent application EP-A-O 080 348 (which corresponds to U.S. Pat. No. 4,428,378) —such that this time interval is shortened with increasing physical activity. The teachings of EP-A-O- 080 348 and U.S. Pat. No.

4,428,378 are fully incorporated herein by reference to the extent permitted. The stimulation time interval between a lower limit (resting pulse) and an upper limit (maximum heartbeat frequency) that are selected corresponding to the requirements of the respective living being.

The heart pacemaker 1 has an additional write-read memory (RAM) 51 that, just like the RAM 7, is connected to the microprocessor 5 via the address line 11 and via the control line 13. The RAM 51 is subdivided into four memory segments 51a, 51b, 51c, and 51d that are separately addressable by the microprocessor 5.

The RAM 51 is provided for storage of the digital output data of the analog-to-digital converter 46 that correspond to the chronological curve of the signal of the piezoelectric sensor 42 during a defined time span. To this end, the microprocessor 5 can switch the RAM 51, whose data line 52 is connected to the line 47, into a write mode via appropriate control signals over the control line 13. In order for this to occur, a corresponding instruction must be telemetrically transmitted to the heart pacemaker 1 on the basis of suitable actuation of the keyboard 37 of the PC 36.

The RAM 51 can also be switched into a read mode, during which the data stored in the RAM 51 can be telemetrically transmitted into the RAM 7 of the PC 36 at any time upon a suitable actuation of the keyboard 37 of the PC 36.

When, in read mode, as in the case of the illustrated embodiment, the data stored in the RAM 51 are transmitted to the microprocessor 5 via the same line 47 via which the digital output data of the analog-to-digital converter 46 are normally supplied to the microprocessor 5, it must be assured, in order to avoid disturbances, that no data be supplied from the output of the analog-to-digital converter 46 onto the line 47, at least as long as the RAM 51 is in read mode. This, for example, can be accomplished in that the microprocessor 5 inhibits the signal editing circuit 44 from producing an output by supplying appropriate data to the digital-to-analog interface 49. In a way not shown, however, it is also possible to disconnect the output of the analog-to-digital converter 46 from the line 47 or to directly inhibit the analog-to-digital converter 46 from producing an output.

When the data stored in the RAM 51 correspond to a time span in which the living being was subjected to a defined physical stress and when PC 36 is programmed such that it is in the position to simulate the setting of the time interval that defines the stimulation frequency in the fashion that the microprocessor 5 of the heart pacemaker 1 would undertake with a given programming, there is thus a possibility of displa_ing the stimulation frequency on the monitor 38 of the PCM 36 as a function of the physical activity of the living being.

An attending physician is then in the position to determine what programming of the heart pacemaker 1 corresponds to the requirements of the respective living being. In case the physician considers modification of the programming necessary, he can first simulate the effects thereof on the PC 36 before reprogramming the heart pacemaker.

The illustrated heart pacemaker 1 offers the advantage that the transmission/reception coil 41 of the telemetry circuit 40 connected to the PC 36 has to be situated in the proximity of the living being wearing the heart pacemaker 1 only when the RAM 51 is switched into the write mode or the read mode and the telemetric transmission of data to and from, respectively, the RAM 51 takes place. It can be appreciated that, thus, there are no restrictions on the freedom of mobility of the living being while the living being wearing the heart pacemaker is subjected to a physical stress. Moreover, the data stored in the RAM 51 are available at any time without the living being having to be subjected to another physical stress.

As already mentioned, the RAM 51 is subdivided into four memory segments 51a, 51b, 51c, and 51d. These segments can be separated from one another in the way set forth above for the entire RAM 51 and can be switched into the write mode at various points in time for storing data. There is thus the possibility of storing data corresponding to the chronological curve of the signal of the piezoelectric sensor 42 for a plurality of defined time spans. This is particularly advantageous when there are physical stresses during the corresponding time spans that deviate from one another in terms of their intensity and their chronological course.

The RAM 51 or, respectively, the memory segments 51, 51b, 51c, and 51d thereof, preferably contains a plurality of memory cells having a defined bit width that are individually addressable by the microprocessor 5. The memory cells of the overall RAM 51 or, respectively, of one of the memory segments 51a, 51b, 51c, or 51d are addressed once in a defined sequence after switching into the write mode, wherein the defined sequence is usually the sequence according to the address numbers. The length of the defined time span during which data corresponding to the chronological course of the signal of the piezoelectric sensor 42 can be stored thus corresponds to that time duration that elapses until all memory cells of the entire RAM 51 or, respectively, one of its memory segments 51a, 51b, 51c, or 51d are addressed once. After switching into the read mode, the memory cells of the overall RAM 51 or, respectively, of a memory segment 51a, 51b, 51c, or 51d are again addressed in the defined sequence, whereby the telemetric transmission of the data to the PC 36 ensues simultaneously.

If desired, however, there is also the possibility, by suitable actuation of the keyboard 37 of the PC 36, of telemetrically causing the microprocessor 5 to modify the addressing just set forth so that the defined sequence in which it addresses the memory cells of the RAM 51 or, respectively, of one of the memory segments 51a, 51b, 51c, or 51d, after switching into the write mode, is cyclically and continuously repeated until a switch is made from write mode to read mode. After switching into the read mode, the microprocessor 5—beginning with that memory cell that follows the memory cell addressed last in the write mode—addresses all of the memory cells once in accordance with the defined sequence for telemetric transmission of the corresponding data to the PC 36. In the addressing just set forth, thus, those data are always stored that relate to a defined time span that extends chronologically back proceeding from a given time and whose chronological duration again corresponds to the time required for the addressing of the participating memory cells.

As an example, the RAM 51 can comprise a total of 1024 memory cells each having a bit width of eight bits. The memory segments 51a, 51b, 51c, and 51d can each comprise 256 memory cells. When the signal of the piezoelectric sensor is sensed at intervals of one second and is converted into corresponding digital data by the analog-to-digital converter 46, data regarding a time span of at most about 17 minutes can be stored. However, there is also the possibility of storing data from four different time spans of about four minutes duration each in the individual memory segments 51a, 51b, 51c, and 51d.

When the addressing of the memory cells ensues in the way first set forth, i.e. each memory cell is only addressed a single time after switching into the write mode, the microprocessor 5—when addressing the entire RAM 51 beginning with the memory cell having the address number zero—addresses all memory cells in the sequence of their address number up to address number 1023. When only individual memory segments 51a, 51b, 51c, and 51d are addressed, this analogously applies to the memory cells having the address numbers 0–255, 256,–511, 512–667 and 768–1023. After switching the RAM 51 or, respectively, a memory segment 51a, 51b, 51c, or 51d into the read mode for telemetric transmission of the stored data, the corresponding addressing process is repeated.

In the case of the second addressing mode set forth for the entire RAM 51 (and analogously to the individual memory segments 51a, 51b, 51c, and 51d), the addressing procedure in the write mode does not end with the addressing of the memory cell having the address number 1023. On the contrary, the addressing procedure is repeated cyclically until that time at which the RAM 51 is switched into the read mode for telemetric transmission of the stored data. Thus, data with respect to the last 17 minutes can be stored under the condition that the addressing cycle has already been completely run through once at this time. When, for example, the memory cell having the address number 563 was the last memory cell addressed preceding switching into the read mode, the addressing cycle in the read mode continues with the memory cells having the address number 564. The addressing initially continues up to the memory cell having the address number 1023 and then beginning with the memory cell having the address number 0, is continued up to the memory cell having the address number 563. All memory cells are then addressed in the read mode in the same sequence as they were previously addressed in the write mode so that a complete telemetric transmission of the stored data is capable of being carried out.

In the illustrated medical device, the pacemaker 1, a special RAM 51 can be provided for storing data corresponding to the chronological curve of the signal of the piezoelectric sensor 42. This is not absolutely necessary since the storing of these data can also ensue in the write-read memory RAM 7 in a memory area reserved for this purpose.

It can be appreciated that while the memory segments 51a, 51b, 51c, and 51d are illustrated as separate memory modules, this is to be only an example since memory segments corresponding to the memory segments 51a, 51b, 51c, and 51d can also be realized via software.

It should also be understood that the external data processing means need not necessarily be a PC, but, on the contrary, other suitable devices, for example, programmers that are standard in conjunction with heart pacemakers, can be used.

Yet further, it should also be understood that a signal corresponding to the physical activity of the living being can also be obtained via a sensor other than the illustrated piezoelectric sensor 42. For example, a sensor for measuring the body temperature of the living being can be used.

While a preferred embodiment has been shown, modifications and changes may become apparent to those skilled in the art which shall fall within the spirit and scope of the invention. It is intended that such modifications and changes be covered by the attached claims.

I claim:

1. A device that is implantable into a body of a living being, comprising:
   means for stimulating a physiological event of said living being with a variable stimulation intensity;
   adjustment means operatively coupled to said means for stimulating for adapting the stimulation intensity to physical activity of said living being;
   sensor means operatively coupled to said adjustment means for generating a signal corresponding to physical activity of said living being, said adjustment means adapting the stimulation intensity in view of said signal generated by said sensor means;
   memory means for storing digital data which is selectively operable between read and write modes;
   means for entering in said memory means said digital data corresponding to a chronological curve of said signal generated by said sensor means over a time span; and
   means for recalling said digital data stored in said memory means and telemetrically transmitting said data to an external data processing means.

2. The device of claim 1, comprising means for telemetrically selecting operation of said memory means in said read or write mode via an external device.

3. The device of claim 1, wherein said memory means comprises a plurality of individually addressable memory cells and said device includes means for addressing said cells in a defined sequence when said memory is operated in its write or read mode.

4. The device of claim 3, wherein said addressing means addresses said memory cells only once each in said read and write modes.

5. The device of claim 3, wherein said addressing means addresses said memory cells repeatedly in said read and write modes.

6. The device of claim 1, wherein said memory means comprises a plurality of memory sectors, each of which is separately addressable via telemetric signals, each sector storing digital data corresponding to a chronological curve of said signal generated by said sensor means over a defined time span.

7. The device of claim 1, wherein said device is a heart pacemaker and said means for stimulating stimulates the heart of said living being.

8. The device of claim 3, wherein said addressing means is telemetrically programmable.

9. A medical system, comprising a device that is implantable into a body of a living being and external data processing means telemetrically coupled to said device, wherein:
   said device that is implantable into a body of a living being includes means for stimulating a physiological event of said living being with a variable stimulation intensity; programmable adjustment means operatively coupled to said means for stimulating for adapting the stimulation intensity to physical activity of said living being; sensor means operatively coupled to said adjustment means for generating a signal corresponding to physical activity of said living being, said adjustment means adapting the stimulation intensity in view of said signal generated by said sensor means; memory means for storing digital data which is selectively operable between read and write modes; means for entering in said memory means said digital data corresponding to a chronological curve of said signal generated by said sensor means over a time span; and means for recalling said digital data stored in said memory means and telemetrically transmitting said digital data to said external data processing means; and said data processing means telemetrically coupled to said device includes means for receiving said digital data from said device; means for simulating the stimulation by said device in view of said digital data received from said device; and means for telemetrically reprogramming said adjustment means.

* * * * *